(12) United States Patent
Montero Casimiro et al.

(10) Patent No.: US 8,435,521 B2
(45) Date of Patent: May 7, 2013

(54) PHARMACEUTICAL COMPOSITIONS CAPABLE OF INDUCING APOPTOSIS IN TUMOUR CELLS, USEFUL FOR DIAGNOSIS AND TREATMENT OF B-CHRONIC LYMPHOCYTIC LEUKAEMIA

(75) Inventors: Jose Enrique Montero Casimiro, Havanah (CU); Ruby Alonso Ramirez, Havanah (CU); Rolando Perez Rodriguez, Havanah (CU)

(73) Assignee: Centro de Immunolgia Molecular (CU)

( * ) Notice: Subject to any disclaimer, the term of this patent is extended or adjusted under 35 U.S.C. 154(b) by 491 days.

(21) Appl. No.: 12/525,449

(22) PCT Filed: Dec. 24, 2007

(86) PCT No.: PCT/CU2007/000022
§ 371 (c)(1),
(2), (4) Date: Oct. 14, 2009

(87) PCT Pub. No.: WO2008/077356
PCT Pub. Date: Jul. 3, 2008

(65) Prior Publication Data
US 2010/0047242 A1 Feb. 25, 2010

(30) Foreign Application Priority Data
Dec. 26, 2006 (CU) .................................. 2006-0249

(51) Int. Cl.
*A61K 39/395* (2006.01)
(52) U.S. Cl.
USPC .................................... 424/141.1; 424/144.1
(58) Field of Classification Search ........................ None
See application file for complete search history.

(56) References Cited

U.S. PATENT DOCUMENTS 6,372,215 B1 * 4/2002 Starling et al. ............. 424/141.1
6,572,857 B1 6/2003 Casimiro et al.

OTHER PUBLICATIONS

Dillman, Annals of Internal Medicine, 1989 111:592-603.*
Osorio et al, Blood, 1997, 30:89:2833-2841.*
Larrick, J.W. and Gavilondo, J.; Meeting Report: Therapeutic antibody technology 97. Immunotechnology. Jan. 1998, vol. 3, pp. 303-307.
Ibanez A. et al. Mitogen-Activated Protein Kinase Pathway Activation by the CD6 Lymphocyte Surface Receptor. Journal of Immunology, Jul. 2006, vol. 177, pp. 1152-1159.
Singer, N.G. et al. CD6: Expression During Development, Apoptosis and Selection of Human and Mouse Thymocytes. International Immunology, Jun. 2002, vol. 14 No. 6, pp. 585-597.

* cited by examiner

*Primary Examiner* — Mark Halvorson
(74) *Attorney, Agent, or Firm* — Marianne Fuierer; Moore & Van Allen, PLLC

(57) ABSTRACT

The present invention is related to the branch of immunology and particularly with the generation of pharmaceutical compositions comprising a humanized monoclonal antibody recognizing the leukocyte differentiation antigen CD6. Accordingly with that statement, the purpose of this invention is to provide pharmaceutical compositions comprising a humanized anti-CD6 monoclonal antibody for the diagnosis and treatment of Lymphoproliferative Syndromes and particularly the B-Cell Chronic Lymphocytic Leukemia. The essence of the invention consist in the application of a humanized Monoclonal Antibody that recognizes the CD6 antigen, the generation of pharmaceutical compositions comprising that antibody being able to induce apoptosis of malignant cells from B-Cell Chronic Lymphocytic Leukemia patients, reaching a clinical and a histological antitumor efficacy. The field of application of the present invention extends to the Oncology.

5 Claims, 3 Drawing Sheets a) Peripheral blood b) Bone Marrow

PHARMACEUTICAL COMPOSITIONS CAPABLE OF INDUCING APOPTOSIS IN TUMOUR CELLS, USEFUL FOR DIAGNOSIS AND TREATMENT OF B-CHRONIC LYMPHOCYTIC LEUKAEMIA

CROSS-REFERENCE TO RELATED APPLICATIONS

This application is filed under the provisions of 35 U.S.C. §371 and claims the priority of International Patent Application No. PCT/CU2007/000022 filed on Dec. 24, 2007, which in turn claims priority of Cuban Application No. 2006-0249 filed on Dec. 26, 2006, the contents of which are incorporated by reference herein for all purposes.

FIELD OF THE INVENTION

The present invention relates to pharmaceutical compositions comprising a humanized Monoclonal Antibody recognizing the leukocyte differentiation antigen CD6 able to induce apoptosis in tumor cells, useful for the treatment of B-Cell Chronic Lymphocytic Leukemia.

DESCRIPTION OF THE PRIOR ART

Therapeutic relevance of Monoclonal Antibodies (MAb) has been validated in the medical practice. Particularly in cancer, MAbs belong to the current therapeutic armamentarium in patients with different kind of tumors (Weiner, L. M. et al. (2006) Hum Antibodies 15(3):103; Imai, K. et al. (2006) Nat Rev Cancer 6(9):714).

Apoptosis is a natural biological mechanism of cell death; however it can be induced therapeutically. Apoptosis represent a relevant way to reach the tumor cell growth control and constitute a mechanism of action claimed for several medicines, including MAbs with therapeutic use in patients with several kinds of tumors. Consequently, the search for drugs with the capacity to promote cell death mediated by apoptosis becomes relevant for medical oncology (Cartron, G. et al. (2004) Blood 104:2635). Lymphoproliferative syndromes and particularly B-Cell Chronic Lymphocytic Leukemia (B-CLL) constitute a contemporary health problem. B-CLL is the leukemia with the highest prevalence in the western world and there is not available a therapeutic drug with curative effects (Chiorazzi, N. et al. (2005) N Engl J Med 352(8): 804; Herishanu, Y. et al. (2005) Transfus Apher Sci 32(1):85). Currently, the use of mAbs able to eliminate the tumor cells is a relevant therapeutic option in those patients (Robak, T. (2005) Transfus Apher Sci 32(1):33). Nevertheless a major disadvantage for this approach, based on the use of specific MAbs to CD52 and CD20, results in its very limited anti-tumor therapeutic effect inducing also the elimination of normal lymphocytes of the individual. (Nuckel, H. et al. (2005) Eur J Pharmacol 514(2-3):217; Cartron, G. et al. (2004) Blood 104:2635). Lack of specific recognition promotes a prolonged lymphopenia constituting a risk factor for a frequent emergence of infections in treated patients, which are already sensitive to them due to the inherent characteristics to this cancer (Boye, J. et al. (2003) Ann Oncol 14(4):520; Cartron, G. et al. (2004) Blood 104:2635; Potter, M. (1999) 12(4):359; Ravandi, F. et al. (2006) Cancer Immunol Immunother 55(2):197).

Tumor cells from B-CLL patients express cell surface markers characteristic of normal B lymphocytes (e.g.: CD19 y el CD20). Particularly, emergence of tumor cells has been associated to B lymphocytes from peripheral blood that co-express the leukocyte differentiation antigen CD5 (Herishanu, Y. et al. (2005) Transfus Apher Sci 32(1):85). CD5 is a distinctive marker for B-CLL but not definitive, because it may only represent a circumstantial marker of a tumor cell subpopulation in peripheral blood, and it is still elusive if those are originated in the bone marrow or proceed from an extra-medullar source (Caligaris-Cappio, F. et al. (2004) Hematol Oncol Clin N Am 18:849).

The leukocyte differentiation antigen CD6 is a molecule limitedly studied and is poorly characterized. CD6 as a surface glycoprotein is primarily expressed in T lymphocytes. It is basically considered that in those cells constitute a receptor with co-stimulatory functions, but the underlying mechanism is known (Aruffo, A. et al. (1997) Immunol Today 18 (10): 498; Patel, D. D. (2000) J Biol Regul Homeost Agents 2000 14(3):234). CD6 expression in mature thymocytes has been associated to their resistance to apoptosis during the lymphocytes maturation process in that lymphoid organ (Singer N. G. et al. (2002) Int Immunol. 14(6):585). Interestingly, CD6 molecule is expressed in a minor subpopulation of B lymphocytes from peripheral blood of normal individuals, but there is a limited understanding on the origin and the functional characterization in those cells. Additionally, peripheral blood mononuclear cells from B-CLL patients also express the CD6 molecule. It is considered that CD6 molecule is co-expressed with the CD5 molecule, but differently to that molecule, CD6 has been only eventually analyzed in samples from B-CLL patients.

Furthermore, the recognition of the CD5 molecule with specific Monoclonal Antibodies induce apoptosis in tumor cells from B-CLL patients, but only in a subgroup of them (Pers, J. O. et al. (2002) Leukemia 16:44).

The CD6 molecule is recognized by the murine MAb ior-t1A. In a previous study with samples from B-CLL patients was found that the murine MAb ior-t1A inhibits the apoptosis induced by an anti-lgM antibody in B lymphocytes. (Osorio, L. M. et al. (1997) Blood, 89(8):2833). On the other hand, therapeutic compositions of this murine anti-CD6 MAb have therapeutic effect in Psoriasis (Montero, E. et al. (1999) Autoimmunity 29(2):155).

Subsequently, using genetic engineering methods (EP 0699755) it was obtained a humanized version from that murine anti-human CD6 MAb, designated T1h (EP 0807125).

Using the humanized MAb T1h we found that recognizes the CD6 molecules expressed in tumor cells from peripheral blood and surprisingly, also on bone marrow cells from B-CLL patients. Moreover, T1h MAb also recognizes tumor cells that do not express the CD5 molecule making the CD6 a tumor marker including the CD5 subpopulation. Moreover, the humanized Monoclonal Antibody T1h induces apoptosis in tumor cells from B-Cell Chronic Lymphocytic Leukemia patients but not in normal lymphocytes.

The novelty of the present invention consist in the generation of therapeutic compositions comprising anti-CD6 Monoclonal Antibodies for their application in patients with Lymphoproliferative Syndromes and particularly in B-Cell Chronic Lymphocytic Leukemia patients. Surprisingly, the recognition of the CD6 molecule with the humanized Monoclonal Antibody T1h induce apoptotic cell death in tumor cells from patients with Lymphoproliferative Syndromes expressing the CD6 molecule and particularly in tumor B lymphocytes from B-Cell Chronic Lymphocytic Leukemia patients, which lead to the therapeutic use of T1h MAb in this kind of tumors. In addition, T1h MAb treatment may sensitize malignant cells to the effect of cytotoxic drugs which may facilitate the combinatorial use of the humanized Monoclonal Antibody T1h with radiotherapy, chemotherapeutic agents or other biotherapies.

DETAILED DESCRIPTION OF THE INVENTION

The present invention relates to therapeutic compositions of Monoclonal Antibodies that recognize the human antigen CD6, effective in the treatment of patients with Lymphoproliferative Disorders. More particularly, the present invention comprises the use of pharmaceutical compositions comprising the humanized Monoclonal Antibody T1h, which recognizes the human leukocyte differentiation antigen CD6 and their use for the diagnosis and treatment of the B-Cell Chronic Lymphocytic Leukemia.

The term "humanized Monoclonal Antibody" refers to a Monoclonal Antibody obtained by genetic engineering methods as described in the patent No. 0699755 (E. P. Bul). It is a subject of the present invention a therapeutic composition comprising the humanized MAb T1h obtained from the hybridoma IOR-T1A with deposit No. ECACC 96112640, deposited in the European Collection of Cell Cultures filed on Nov. 26, 1996, able to induce apoptosis in malignant cells from B-Cell Chronic Lymphocytic Leukemia patients through the recognition of the CD6 molecule, alone or in combination with any of the selected agents from the group of:

Chemotherapeutic agents such as Fludarabine
Monoclonal Antibodies specific to surface molecules of malignant lymphocytes such as anti-CD20 antibodies.

Pharmaceutical compositions of the present invention also comprise an appropriate excipient that would be a physiological buffered solution, and it would be administered in the way of injections in a range of doses from 0.05 to 1 mg/Kg of body weight. On the other hand, the present invention relates to a diagnostic reagent comprising the anti-CD6 Monoclonal Antibody to be used for the diagnosis of the B-Cell Chronic Lymphocytic Leukemia.

1. Generation of pharmaceutical compositions comprising the humanized anti-human CD6 Monoclonal Antibody T1h.

The humanized anti-human CD6 Monoclonal Antibody T1h was obtained from the hybridoma IOR-T1A with deposit No. ECACC 96112640, as described in (EP 0 807 125 A2). The pharmaceutical composition of the present invention comprises the humanized Monoclonal Antibody T1h additionally; this composition comprises as an appropriate excipient a physiological buffered solution, similar to others used for therapeutic Monoclonal Antibodies for intravenous use, as described in EP 0807125. The composition of the present invention is administered in the way of injections in a range of doses from 0.05 to 1 mg/Kg of body weight 2. Characterization of the specific recognition of the humanized Monoclonal Antibody T1h.

Peripheral blood mononuclear cells and bone marrow cells from B-Cell Chronic Lymphocytic Leukemia patients are stained with an antihuman CD19 MAb FITC-conjugated. Afterwards, cells are incubated with the following Monoclonal Antibodies: anti-human CD6 Monoclonal Antibody conjugated to biotin (T1h) or anti-human CD5 conjugated to PE-Cy5 (Pharmingen) or anti-human CD20 conjugated to biotin (Rituximab-Rx). The binding of biotinylated antibodies is detected with a Streptavidin, PE-Cy5.5 conjugate. At least 10 000 living cells are acquired in a Flow Cytometer FACScan. Dead cells are excluded with the Propidium Iodine staining.

3. Characterization of the antitumor effect of the humanized Monoclonal Antibody T1h on cells from B-Cell Chronic Lymphocytic Leukemia patients.

Peripheral blood mononuclear cells from normal individuals or from B-Cell Chronic Lymphocytic Leukemia patients are treated in vitro with 0.1 µg/mL of the humanized Monoclonal Antibody T1h or an isotype control (R3h Monoclonal Antibody) during 18$h$ at 37° C. and 5% of $CO_2$. Then, cells are washed and incubated with Annexin V conjugated to FITC for 10 min at room temperature. Afterward, cells are stained with Propidium Iodine (PI) and acquired in a Flow Cytometer FACScan. Apoptotc cells are defined as Annexin V+/PI−.

EXAMPLES

The following examples are intended to illustrate the invention. The humanized anti-human CD6 Monoclonal Antibody T1h was obtained from the hybridoma IOR-T1A with deposit No. ECACC 96112640, as described in (EP 0 807 125 A2).

Example 1

The humanized anti-human CD6 Monoclonal Antibody T1h recognizes the malignant cells from the peripheral blood of B-Cell Chronic Lymphocytic Leukemia patients.

It was evaluated the T1h MAb recognition in peripheral blood mononuclear cells from 19 B-Cell Chronic Lymphocytic Leukemia patients and determined the expression of the CD6 molecule on B cells defined by the CD19 and CD20 markers. Moreover, it was compared the expression of those cell markers with samples from normal individuals (FIG. 1). The study was performed by flow cytometry using a FACScan to analyze the samples. Normal values are depicted as red filled squares in FIG. 1.

Example 2

The humanized anti-human CD6 Monoclonal Antibody T1h recognizes the malignant cells from the bone marrow of B-Cell Chronic Lymphocytic Leukemia patients.

It was evaluated the T1h MAb recognition in peripheral blood mononuclear cells from 4 B-Cell Chronic Lymphocytic Leukemia patients and determined the expression of the CD6 molecule on B cells defined by the CD19 and CD20 markers. Moreover, it was compared the expression of those cell markers with samples from normal individuals (FIG. 2). The study was performed by flow cytometry using a FACScan to analyze the samples.

Example 3

The humanized anti-human CD6 Monoclonal Antibody T1h recognizes malignant cells from B-Cell Chronic Lymphocytic Leukemia patients which do not express the CD5 molecule.

It was evaluated the T1h MAb recognition in peripheral blood mononuclear cells (FIG. 3$a$) and bone marrow cells (FIG. 3$b$) from B-Cell Chronic Lymphocytic Leukemia patients and determined the co-expression of the CD6 and the CD5 molecules in malignant cells. Sample 1 represent a patient with CD6+CD5+ tumor cells, and Sample 2 represent a patient with CD6+CD5− tumor cells. The study was performed by flow cytometry using a FACScan to analyze the samples.

Example 4

The humanized Monoclonal Antibody T1h induce apoptotic cell death of malignant cells from B-Cell Chronic Lymphocytic Leukemia patients.

It was evaluated the capacity of the humanized Monoclonal Antibody T1h to induce apoptotic cell death of malignant cells from B-Cell Chronic Lymphocytic Leukemia patients. After the incubation in vitro of the tumor cells with the humanized Monoclonal Antibody T1, it was determined the percent of cells in apoptosis following the criteria that they were positive to the staining with Annexin V and Propidium Iodine staining negative. Dexamethasone (Dex) and Rituximab (Rx, an anti-CD20 Monoclonal Antibody) were used as positive controls. The humanized Monoclonal Antibody R3h (IgG1 isotype, anti-human Epidermal Growth Factor Receptor specific) was used has a negative control. Results (FIG. 4) were compared to the cells without treatment (w/o treatment). The study was performed by flow cytometry using a FACScan to analyze the samples.

Figure 1:
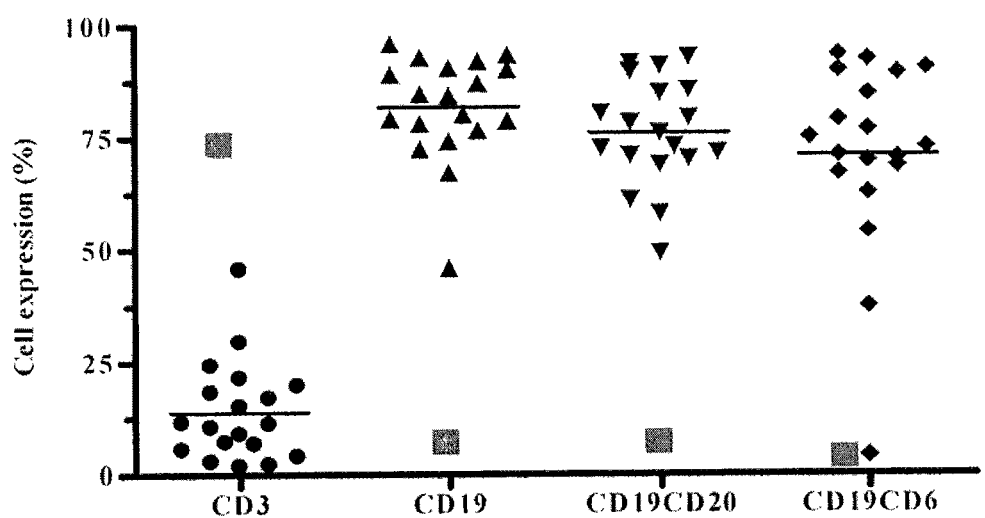
FIG. 1-CD6 expression defined by the humanized Monoclonal Antibody T1h in peripheral blood mononuclear cells from B-Cell Chronic Lymphocytic Leukemia patients. A potential tumor specific antigen.
Figure 2:
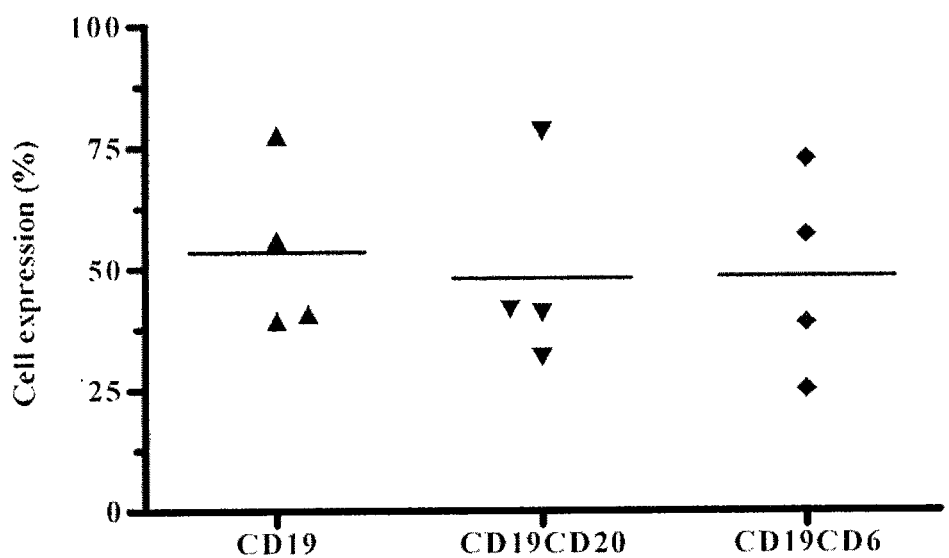
FIG. 2-CD6 expression defined by the humanized Monoclonal Antibody T1h in bone marrow cells from B-Cell Chronic Lymphocytic Leukemia patients. A potential tumor specific antigen.
Figure 3:
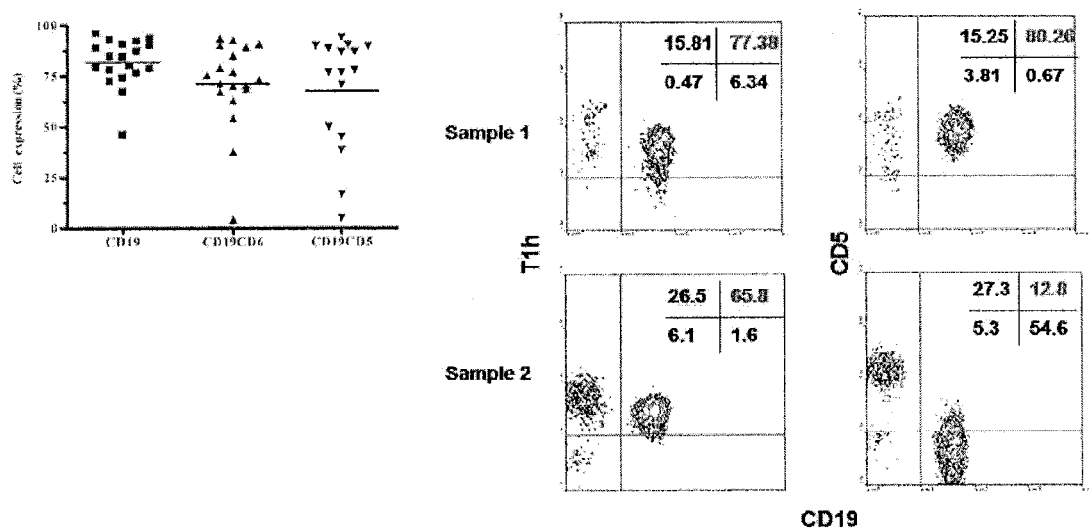
FIG. 3-CD6 expression defined by the humanized Monoclonal Antibody T1h in peripheral blood mononuclear cells from B-Cell Chronic Lymphocytic Leukemia patients which are negative to the expression of the CD5 molecule.
Figure 3:
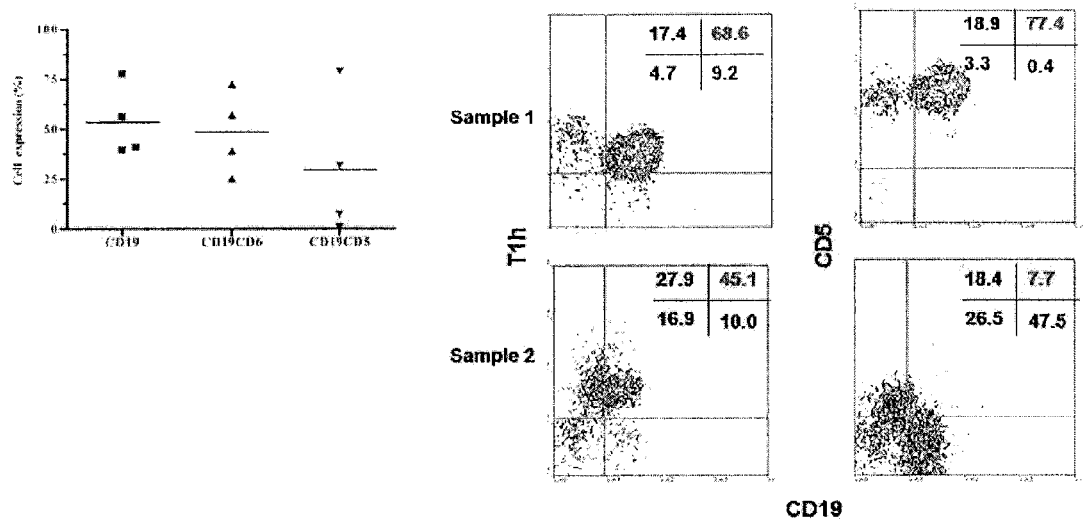
Figure 4:
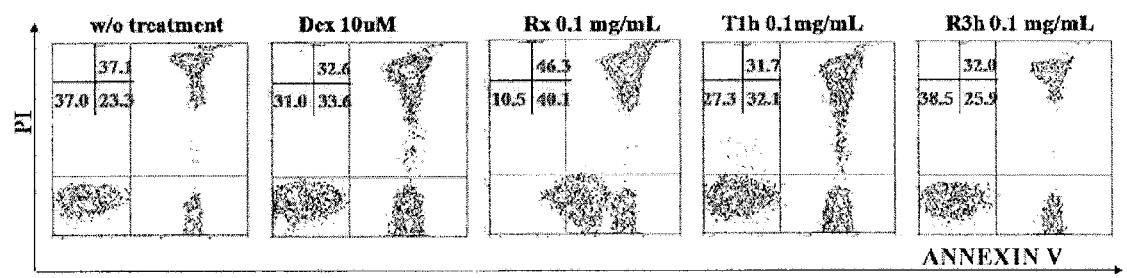
FIG. 4-*Induction* of apoptotic cell death of malignant cells from B-Cell Chronic Lymphocytic Leukemia patients with the humanized Monoclonal Antibody T1h.

The invention claimed is:

1. A method for treating B-Cell Chronic Lymphocytic Leukemia and inducing apoptotic cell death of malignant cells in a subject in need thereof, the method comprising administering to the subject in need thereof an anti-CD6 monoclonal antibody, wherein the anti-CD6 monoclonal antibody is humanized IOR-T1h that is produced by hybridoma IOR-T1A deposited with ECACC as deposit No. ECACC 96112640 and wherein the anti-CD6 monoclonal antibody is in a therapeutic amount to induce apoptotic cell death of the malignant cells.

2. The method of claim 1, wherein the antibody is included in a composition comprising an appropriate excipient.

3. The method of claim 1 wherein the therapeutic amount is at a range of doses of the anti-CD6 Monoclonal Antibody from 0.05 to 1 mg/Kg of body weight.

4. The method of claim 1, wherein the anti-CD6 monoclonal antibody is combined with other cancer treating biotherapies.

5. The method of claim 2, wherein the appropriate excipient is a physiological buffered solution.

* * * * *